(12) United States Patent
Nakanishi et al.

(10) Patent No.: US 10,042,431 B2
(45) Date of Patent: Aug. 7, 2018

(54) INFORMATION PROCESSING APPARATUS, INFORMATION PROCESSING METHOD, AND RECORDING MEDIUM

(71) Applicant: SONY CORPORATION, Tokyo (JP)

(72) Inventors: Yoshihiro Nakanishi, Tokyo (JP); Kosei Yamashita, Kanagawa (JP); Ryo Mukaiyama, Tokyo (JP); Takaomi Kimura, Tokyo (JP); Hideyuki Matsunaga, Kanagawa (JP); Naofumi Fukasawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/907,820

(22) Filed: Feb. 28, 2018

(65) Prior Publication Data
US 2018/0188819 A1   Jul. 5, 2018

Related U.S. Application Data

(63) Continuation of application No. 14/430,991, filed as application No. PCT/JP2013/079612 on Oct. 31, 2013.

(30) Foreign Application Priority Data

Nov. 9, 2012  (JP) .................................. 2012-247885

(51) Int. Cl.
*G09G 5/00*   (2006.01)
*G06F 3/01*   (2006.01)
(Continued)

(52) U.S. Cl.
CPC .............. *G06F 3/017* (2013.01); *A61B 5/743* (2013.01); *G06K 9/00342* (2013.01);
(Continued)

(58) Field of Classification Search
CPC . G06F 3/017; A61B 5/743; A61B 2562/0219; G06K 9/00342; G09G 5/003;
(Continued)

(56) References Cited

U.S. PATENT DOCUMENTS

| 2005/0005308 A1 | 1/2005 | Logan et al. |
| 2007/0195995 A1 | 8/2007 | Matsumoto et al. |

(Continued)

FOREIGN PATENT DOCUMENTS

| JP | 06-142259 | 5/1994 |
| JP | 2000-236466 | 8/2000 |

(Continued)

OTHER PUBLICATIONS

Nov. 7, 2017, Japanese Office Action issued for related JP application No. 2014-545674.

(Continued)

*Primary Examiner* — Peter D McLoone
(74) *Attorney, Agent, or Firm* — Paratus Law Group, PLLC

(57) ABSTRACT

There is provided an information processing apparatus including a data acquiring unit configured to acquire content to which metadata is attached and the metadata attached to the content, the metadata being generated from data obtained from a sensor mounted on a subject, and a display control unit configured to reflect contents of the metadata acquired by the data acquiring unit in display of the content to which the metadata acquired by the data acquiring unit is attached.

17 Claims, 7 Drawing Sheets

(51) Int. Cl.
  *H04N 21/422*    (2011.01)
  *H04N 21/433*    (2011.01)
  *H04N 21/4223*   (2011.01)
  *H04N 21/472*    (2011.01)
  *H04N 9/82*      (2006.01)
  *H04N 21/414*    (2011.01)
  *G06K 9/00*      (2006.01)
  *A61B 5/00*      (2006.01)
  *H04N 21/84*     (2011.01)
  *H04N 21/845*    (2011.01)

(52) U.S. Cl.
  CPC ........... *G09G 5/003* (2013.01); *H04N 9/8205* (2013.01); *H04N 21/41407* (2013.01); *H04N 21/4223* (2013.01); *H04N 21/42201* (2013.01); *H04N 21/4334* (2013.01); *H04N 21/47217* (2013.01); *H04N 21/84* (2013.01); *H04N 21/8456* (2013.01); *A61B 2562/0219* (2013.01)

(58) Field of Classification Search
  CPC ....... H04N 21/41407; H04N 21/42201; H04N 21/4223; H04N 21/4334; H04N 21/47217; H04N 21/84; H04N 21/8456
  See application file for complete search history.

(56) References Cited

U.S. PATENT DOCUMENTS

| | | |
|---|---|---|
| 2011/0305369 A1 | 12/2011 | Bentley et al. |
| 2012/0052972 A1 | 3/2012 | Bentley |
| 2014/0270708 A1* | 9/2014 | Girgensohn ............. H04N 9/79 386/282 |

FOREIGN PATENT DOCUMENTS

| | | |
|---|---|---|
| JP | 2007-226312 | 9/2007 |
| JP | 2007-530151 | 11/2007 |
| JP | 2008-172485 | 7/2008 |
| JP | 2009-297057 | 12/2009 |
| JP | 2012-052845 A | 3/2012 |
| JP | 2012-089909 | 5/2012 |

OTHER PUBLICATIONS

Jul. 18, 2017, CN communication issued for related CN application No. 201380057314.9.

Apr. 14, 2016, European Search Report for related EP Application No. 13853793.1.

* cited by examiner

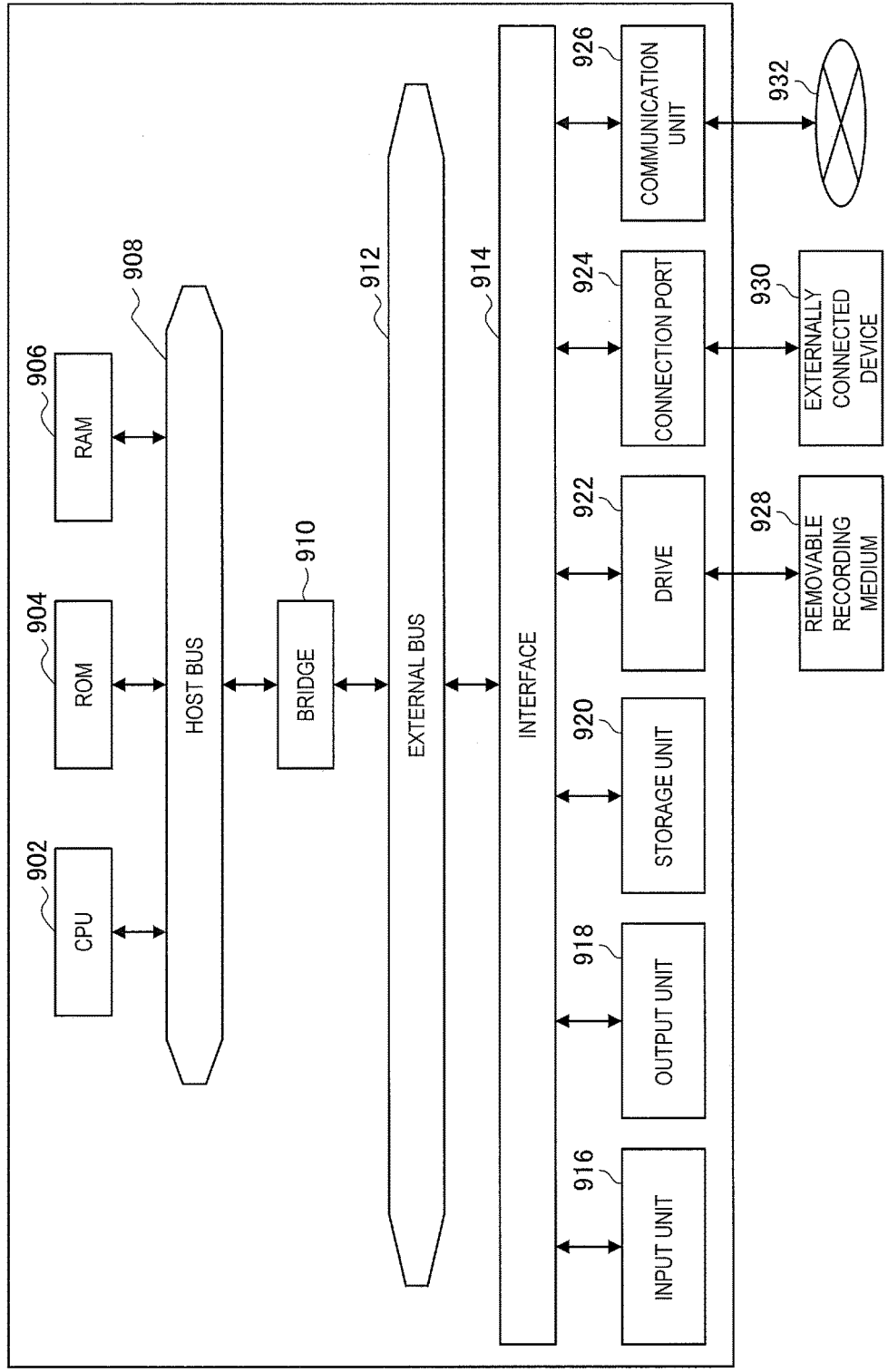

INFORMATION PROCESSING APPARATUS, INFORMATION PROCESSING METHOD, AND RECORDING MEDIUM

CROSS REFERENCE TO PRIOR APPLICATIONS

This application is a continuation of U.S. patent application Ser. No. 14/430,991 (filed on Mar. 25, 2015), which is a National Stage Patent Application of PCT International Patent Application No. PCT/JP2013/079612 (filed on Oct. 31, 2013), which claims priority to Japanese Patent Application No. 2012-247885 (filed on Nov. 9, 2012), which are all hereby incorporated by reference in their entirety.

TECHNICAL FIELD

The present disclosure relates to an information processing device, an information processing method, and a recording medium having a computer program recorded therein.

BACKGROUND ART

Inexpensive digital cameras with high image quality have been widespread, and mobile phones and smartphones in which the digital cameras are embedded also have been widespread. Since the digital cameras have been widespread, it is becoming possible for users to easily take moving images, and opportunities for the users to take moving images are greatly increasing. Especially, it has been widely spread that situations during sports is taken by the digital cameras.

In addition, since capacity of recording medium is increasing and online storage services have been widespread, the number of moving images held by the users is greatly increasing. Accordingly, in order to easily manage the moving images by the user himself/herself, the user generically creates folders, saves the moving images in the folders according to a rule, and manages the moving images.

On the other hand, a technology of acquiring movement of a sport athlete by a sensor mounted on the sport athlete has been disclosed. For example, Patent Literature 1 discloses a technology of mounting sensors on a sport athlete and understanding movement and situations of all sensors via a mobile terminal.

CITATION LIST

Patent Literature

Patent Literature 1: JP 2009-297057A

SUMMARY OF INVENTION

Technical Problem

According to the above-described circumstances, a technology of efficiently viewing a moving image of an athlete playing sports or causing a user to quickly get a desired moving image from among many moving images of the athlete is being desired.

Accordingly, the present disclosure proposes a novel and improved information processing apparatus, information processing method and recording medium having a computer program recorded therein that are capable of mounting a sensor on a subject and controlling, on the basis of metadata, display of content to which the metadata generated by the sensor is attached.

Solution to Problem

According to the present disclosure, there is provided an information processing apparatus including a data acquiring unit configured to acquire content to which metadata is attached and the metadata attached to the content, the metadata being generated from data obtained from a sensor mounted on a subject, and a display control unit configured to reflect contents of the metadata acquired by the data acquiring unit in display of the content to which the metadata acquired by the data acquiring unit is attached.

According to the present disclosure, there is provided an information processing method including acquiring content to which metadata is attached and the metadata attached to the content, the metadata being generated from data obtained from a sensor mounted on a subject, and reflecting contents of the acquired metadata in display of the content to which the acquired metadata is attached.

According to the present disclosure, there is provided a recording medium having a computer program recorded therein, the program causing a computer to execute acquiring content to which metadata is attached and the metadata attached to the content, the metadata being generated from data obtained from a sensor mounted on a subject, and reflecting contents of the acquired metadata in display of the content to which the acquired metadata is attached.

Advantageous Effects of Invention

As explained above, the present disclosure proposes the novel and improved information processing apparatus, information processing method and recording medium having a computer program recorded therein that are capable of mounting a sensor on a subject and controlling, on the basis of metadata, display of content to which the metadata generated by the sensor is attached.

BRIEF DESCRIPTION OF DRAWINGS

FIG. 8 is an explanatory diagram showing a hardware configuration example of an information processing apparatus 100 according to an embodiment of the present disclosure.

DESCRIPTION OF EMBODIMENTS

Figure 1:
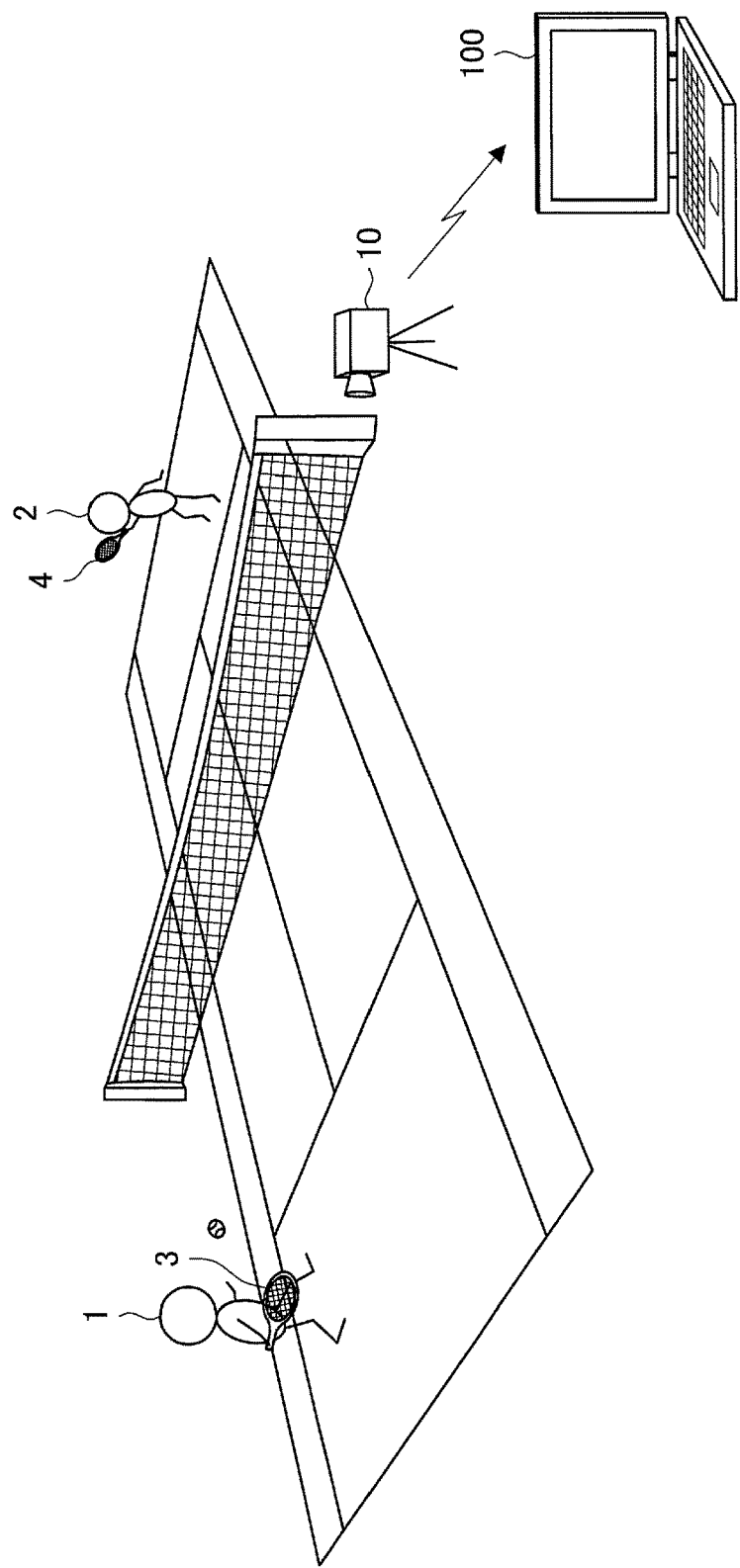
FIG. 1 is an explanatory diagram showing an overview of a system using an information processing apparatus 100 according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description is given in the following order.
<1. Embodiment of Present Disclosure>
[Overview of System]
[Functional Configuration Example of Information Processing Apparatus]
[Operation Example of Information Processing Apparatus]
<2. Hardware Configuration Example>
<3. Conclusion>

1. EMBODIMENT OF PRESENT DISCLOSURE

[Overview of System]

First, with reference to drawings, an overview of a system using an information processing apparatus 100 according to an embodiment of the present disclosure is explained. FIG. 1 is an explanatory diagram showing an overview of a system using the information processing apparatus 100 according to an embodiment of the present disclosure. Hereinafter, with reference to FIG. 1, an overview of the system using the information processing apparatus 100 according to an embodiment of the present disclosure is explained.

As an overview of the system using the information processing apparatus 100 according to an embodiment of the present disclosure, FIG. 1 shows a situation where an imaging apparatus 10 take an image that two athletes 1 and 2 are playing tennis. The imaging apparatus 10 is an apparatus installed to mainly take an image of the athlete 1's play, for example.

The two athletes 1 and 2 have respective rackets 3 and 4, and are playing tennis. Sensors are mounted to the rackets 3 and 4. These sensors can acquire parts of the rackets 3 and 4 hitting balls, power and ball spin rates at a time when the athletes 1 and 2 hit balls, shot types (groundstroke/volley, forehand/backhand, or topspin/slice), swing speeds of the rackets 3 and 4, and swing trajectories. For example, while taking a moving image of the athlete 1 playing tennis, the imaging apparatus 10 generates metadata by using information detected by a sensor mounted on the racket 3 held by the athlete 1, and attaches the metadata to the taken moving image. According to a time axis of the moving image, the imaging apparatus 10 attaches the metadata generated from information detected by the sensor, when attaching the metadata.

According to the example shown in FIG. 1, the sensor is mounted on not the athlete 1 himself who is a subject, but the racket 3 that is equipment used by the athlete 1. However, an embodiment of the present disclosure includes not only the case where the sensor is directly mounted on the athlete 1 but also the case where the sensor is mounted on the equipment used together with the athlete 1, in view of the fact that the equipment is included in the subject.

A diverse sensor is mounted on the racket 3. For example, a pressure sensitive sensor may be used as the sensor mounted on the racket 3. By mounting the pressure sensitive sensor on the racket 3, information such as a part hitting a ball, power and a ball spin rate at a time of hitting the ball can be acquired. For example, an acceleration sensor may be used as the sensor mounted on the racket 3. By mounting the acceleration sensor on the racket 3, for example, change in direction of the racket 3 can be acquired. From the change in direction of the racket 3, information on a type of a stroke can be acquired. In addition, for example, a gyro sensor may be used as the sensor mounted on the racket 3. By mounting the gyro sensor on the racket 3, information on inclination of the racket 3 can be acquired. By acquiring the information on the inclination of the racket 3, information on a swing trajectory of the racket 3 can be acquired. In addition, a microphone may be used as the sensor mounted on the racket 3, for example. By mounting the microphone on the racket 3, sound around the racket can be collected. For example, sound when the racket 3 hits a ball can be collected. From information at a time of collecting the sound when the racket 3 hits the ball, a timing when the racket 3 hits the ball can be acquired.

FIG. 1 also shows the information processing apparatus 100. The information processing apparatus 100 executes a process for displaying the moving image taken by the imaging apparatus 10. The information processing apparatus 100 displays the moving image that the imaging apparatus 10 has taken and to which the metadata is attached, the metadata having been generated by using the information detected by the sensor mounted on the racket 3 held by the athlete 1. Subsequently, when displaying the moving image taken by the imaging apparatus 10, the information processing apparatus 100 acquires the metadata attached to the moving image, and reflects, in the display of the moving image, the information generated from the metadata.

By acquiring the metadata attached to the moving image and by reflecting the information generated from the metadata in display of the moving image, the information processing apparatus 100 according to an embodiment of the present disclosure can present how the athlete 1 who is the subject of the moving image taken by the imaging apparatus 10 has played tennis. The athlete 1 can view the moving image displayed by the information processing apparatus 100, understand good or bad about his play, and use the moving image to improve his skills as an athlete.

With reference to FIG. 1, the overview of the system using the information processing apparatus 100 according to an embodiment of the present disclosure has been explained. Next, a functional configuration example of an information processing apparatus 100 according to an embodiment of the present disclosure is explained.

[Functional Configuration Example of Information Processing Apparatus]

Figure 2:
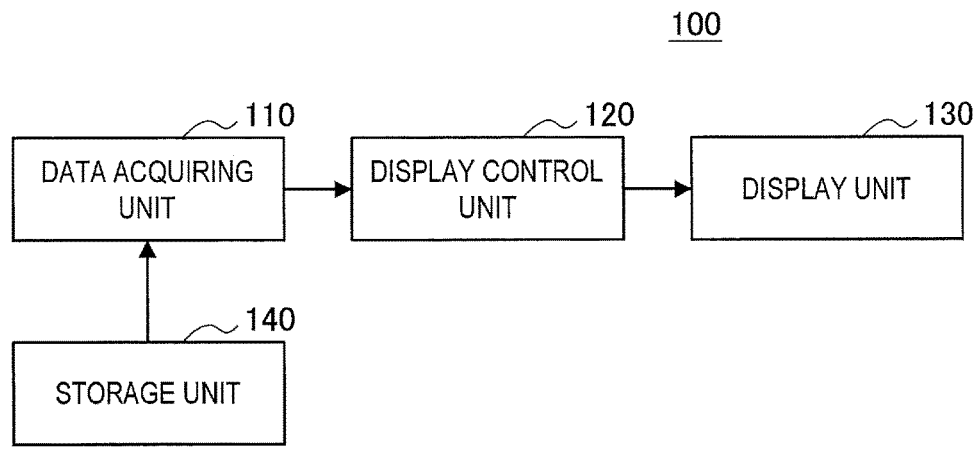
FIG. 2 is an explanatory diagram showing a functional configuration example of an information processing apparatus 100 according to an embodiment of the present disclosure.

FIG. 2 is an explanatory diagram showing the functional configuration example of the information processing apparatus 100 according to an embodiment of the present disclosure. Hereinafter, with reference to FIG. 2, the functional configuration example of the information processing apparatus 100 according to an embodiment of the present disclosure is explained.

As shown in FIG. 2, the information processing apparatus 100 according to an embodiment of the present disclosure includes a data acquiring unit 110, a display control unit 120, and a display unit 130, and storage unit 140.

The data acquiring unit 110 acquires a moving image stored in the storage unit 140. The moving image stored in the storage unit 140 is the moving image that the imaging apparatus 10 has taken and to which the metadata is attached, the metadata having been generated by using the information detected by the sensor mounted on the racket 3 held by the athlete 1. The data acquiring unit 110 acquires the moving image stored in the storage unit 140, and acquires the metadata attached to the moving image.

The moving image to be acquired by the data acquiring unit 110 may be a moving image designated by a user of the information processing apparatus 100, or may be a moving image satisfying a predetermined condition. The data acquiring unit 110 acquires the moving image and the metadata attached to the moving image, and then supplies the acquired moving image and metadata to the display control unit 120.

The display control unit 120 controls display of the moving image acquired by the data acquiring unit 110 on the display unit 130, by using the moving image acquired by the data acquiring unit 110 and the metadata attached to the moving image. In the present embodiment, the display control unit 120 generates information by using the metadata attached to the moving image, and reflects the generated information in the display of the moving image acquired by the data acquiring unit 110.

The display unit 130 displays the moving image acquired by the data acquiring unit 110. The display control unit 120 controls the display of the moving image on the display unit 130. Accordingly, the moving image to be displayed on the display unit 130 is the moving image in which the information generated by the display control unit 120 using the metadata attached to the moving image is reflected. The display unit 130 may be any display device such as a liquid crystal display and an organic electroluminescence display.

The storage unit 140 stores the moving image that the imaging apparatus 10 has taken and to which the metadata is attached, the metadata having been generated by using the information detected by the sensor mounted on the racket 3 held by the athlete 1. The data acquiring unit 110 acquires the moving image stored in the storage unit 140. Note that, with reference to FIG. 2, the information processing apparatus 100 according to an embodiment of the present disclosure internally includes the storage unit 140. However, the present disclosure is not limited thereto. The storage unit 140 for storing the moving image may be installed outside the information processing apparatus 100, and may connect with the information processing apparatus 100 in a wired/wireless manner. In addition, the storage unit 140 may be any recording medium such as a hard disk drive, a solid-state drive, and flash memory.

According to an embodiment of the present disclosure, the information processing apparatus 100 having the configuration shown in FIG. 2 can present how the athlete 1 who is the subject of the moving image taken by the imaging apparatus 10 has played tennis. The athlete 1 can watch the moving image displayed by the information processing apparatus 100, understand good or bad about his play, and use the moving image to improve his skills as an athlete.

The functional configuration example of the information processing apparatus 100 according to an embodiment of the present disclosure has been explained with reference to FIG. 2. Next, an operation example of an information processing apparatus 100 according to an embodiment of the present disclosure is explained.

[Operation Example of Information Processing Apparatus]

Figure 3:
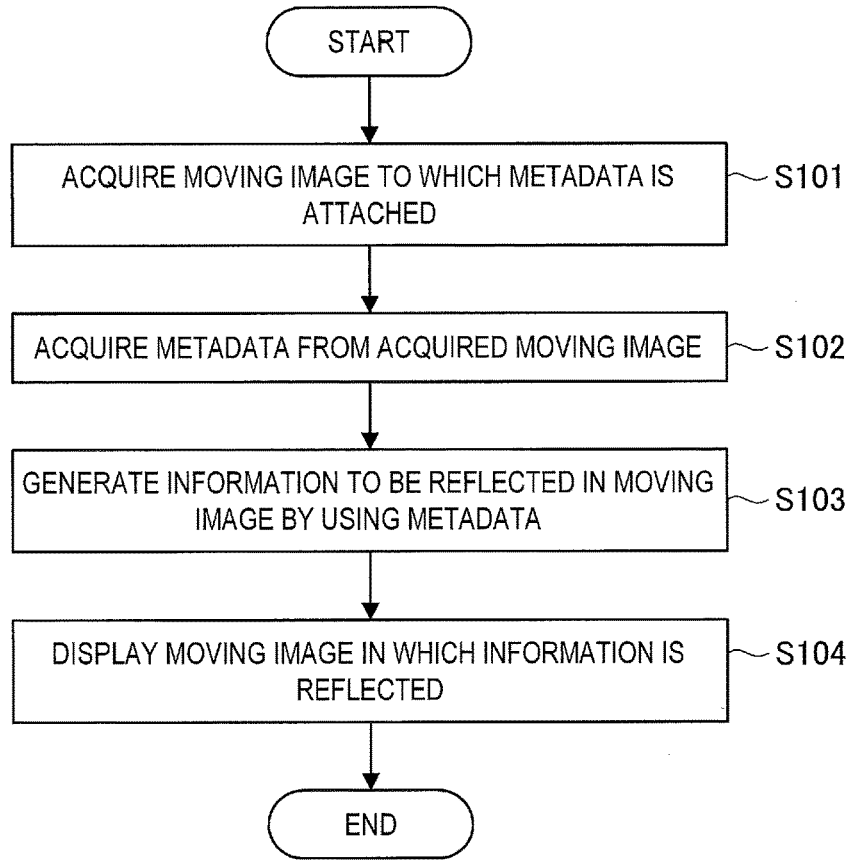
FIG. 3 is a flowchart showing an operation example of an information processing apparatus 100 according to an embodiment of the present disclosure.

FIG. 3 is a flowchart showing the operation example of the information processing apparatus 100 according to an embodiment of the present disclosure. The flowchart in FIG. 3 shows an operation example of the information processing apparatus 100 when the display unit 130 displays the moving image that is stored in the storage unit 140 and to which the metadata is attached. Hereinafter, with reference to FIG. 3, the operation example of the information processing apparatus 100 according to an embodiment of the present disclosure is explained.

First, the information processing apparatus 100 acquires, from the storage unit 140, the moving image that is stored in the storage unit 140 and to which the metadata is attached (Step S101). For example, the data acquiring unit 100 performs the acquisition with regard to the process of Step S101 in which the moving image to which the metadata is attached is acquired.

After the moving image to which the metadata is attached is acquired from the storage unit 140 in Step S101, the information processing apparatus 100 subsequently acquires the metadata from the acquired moving image (Step S102). For example, the data acquiring unit 100 performs the acquisition with regard to the process of Step S102 in which the metadata is acquired.

After the metadata is acquired from the moving image to which the metadata is attached in Step S102, the information processing apparatus 100 subsequently uses the acquired metadata and generates information to be reflected in the moving image when the moving image is displayed (Step S103). For example, the data acquiring unit 100 performs the generation with regard to the process of Step S103 in which the information to be reflected in the moving image when the moving image is displayed is generated. Details of contents of the information generated in Step S103 are explained later with reference to drawings.

After the information to be reflected in the moving image when the moving image is displayed is generated by using the metadata in Step S103, the information processing apparatus 100 subsequently displays, on the display unit 130, the moving image in which the generated information is reflected (Step S104). For example, the display control unit 120 performs the process of Step S104 in which the moving image is displayed on the display unit 130.

By executing the operation as shown in FIG. 3, the information processing apparatus 100 according to an embodiment of the present disclosure can present how the athlete 1 who is the subject of the moving image taken by the imaging apparatus 10 has played tennis. The athlete 1 can watch the moving image displayed by the information processing apparatus 100, understand good or bad about his play, and use the moving image to improve his skills as an athlete.

Here, a display example of the moving image in which the information generated in Step S103 by the information processing apparatus 100 is reflected is shown as an example.

Figure 4:
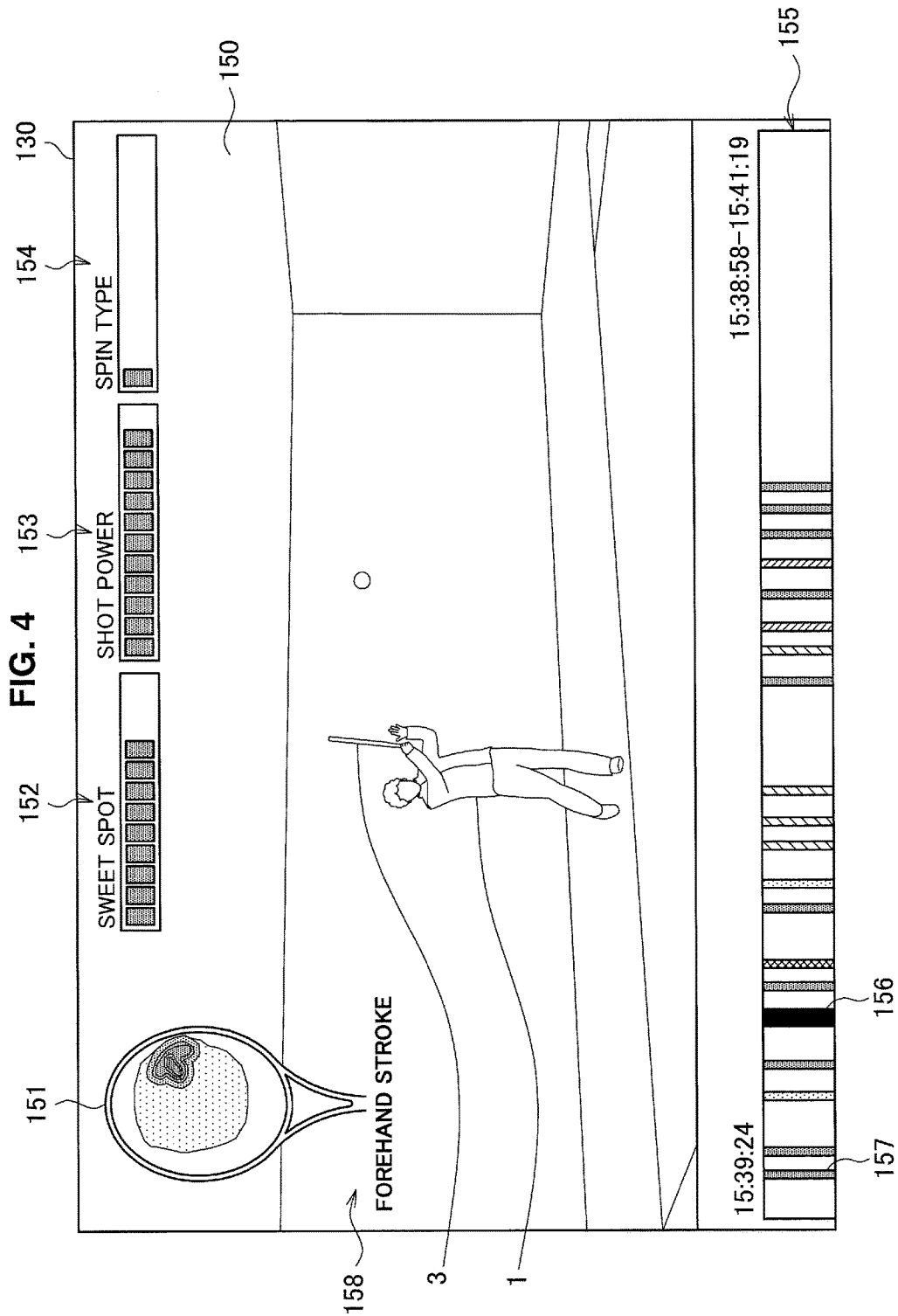
FIG. 4 is an explanatory diagram showing an example of an image displayed on a display unit 130 of an information processing apparatus 100 according to an embodiment of the present disclosure.
Figure 5:
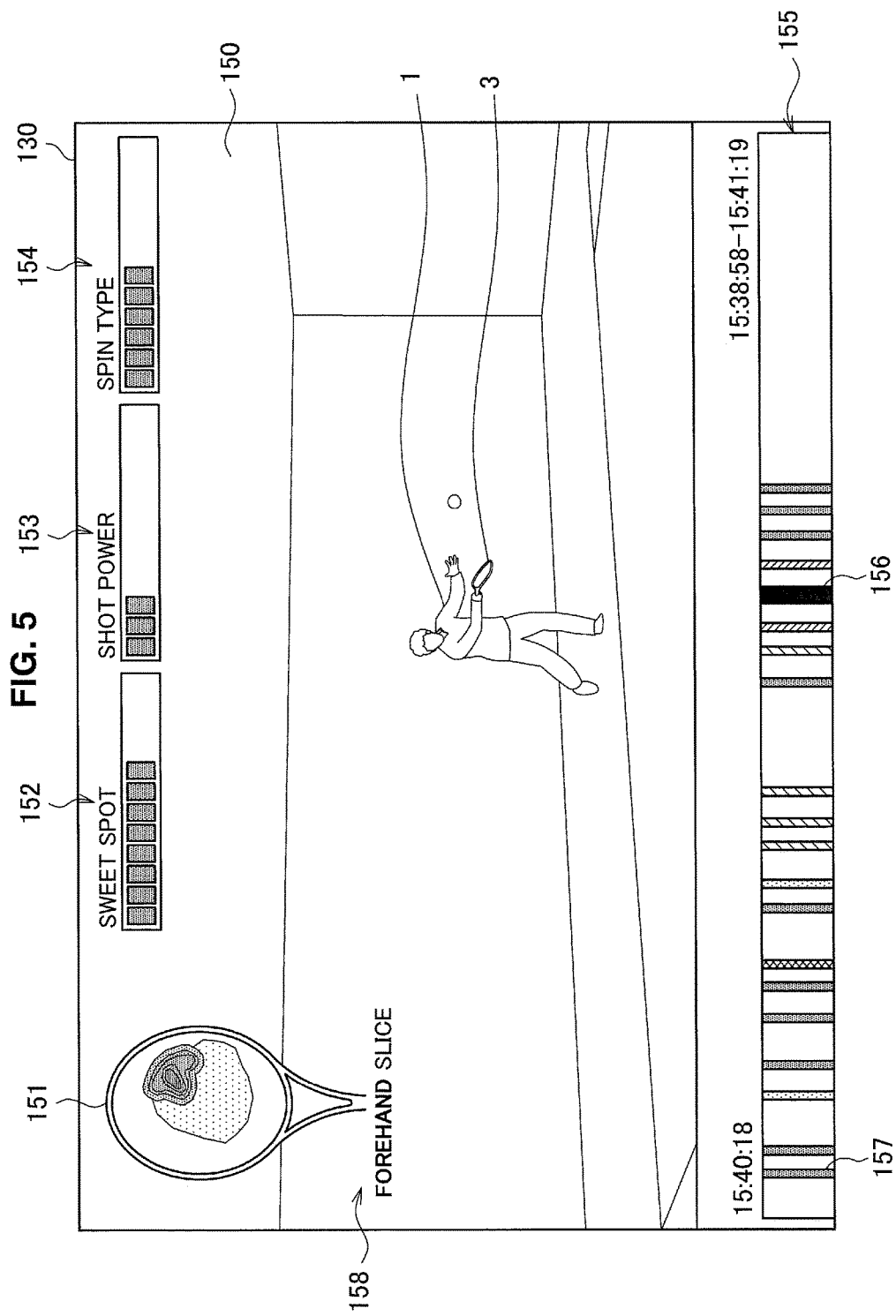
FIG. 5 is an explanatory diagram showing an example of an image displayed on a display unit 130 of an information processing apparatus 100 according to an embodiment of the present disclosure.
Figure 6:
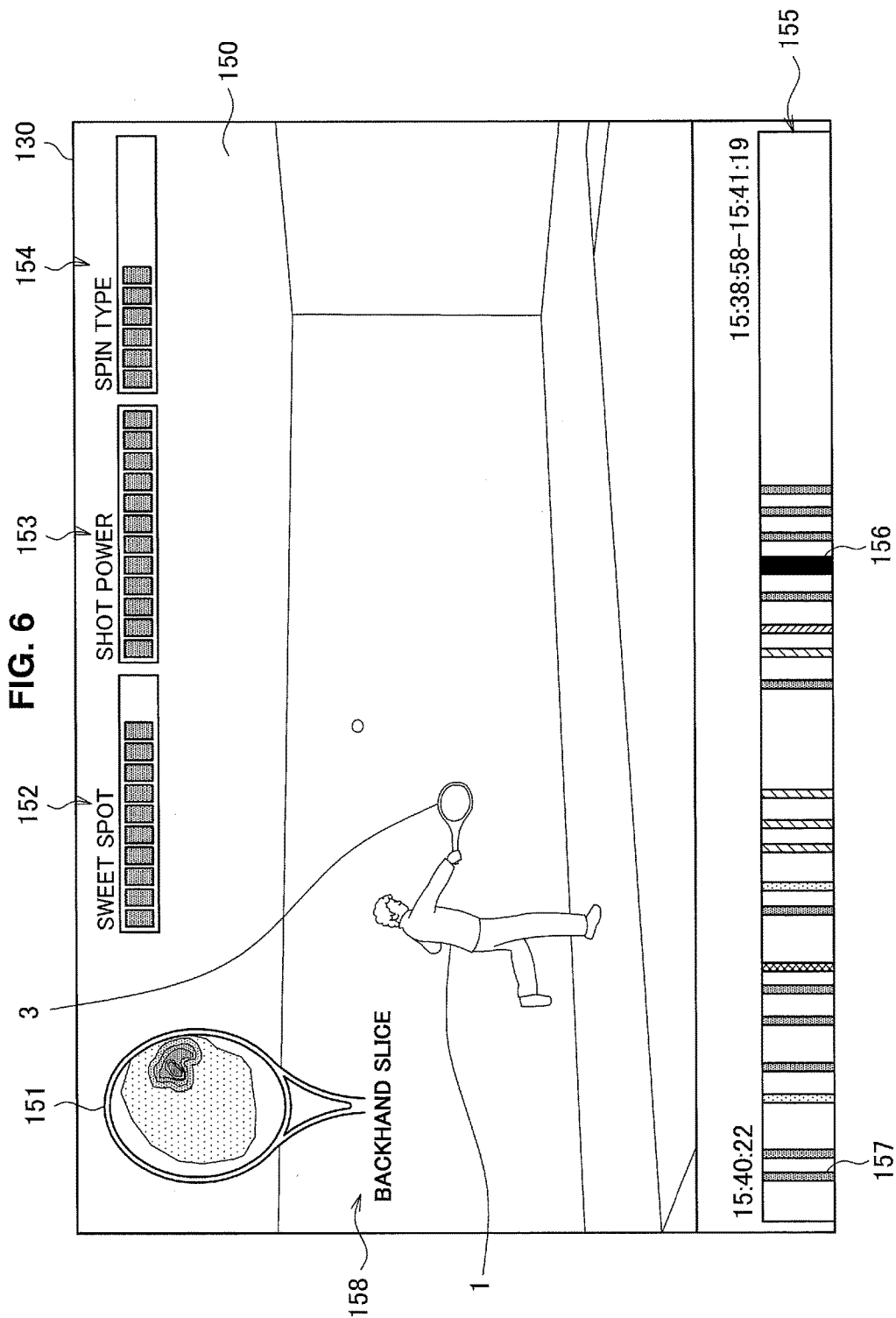
FIG. 6 is an explanatory diagram showing an example of an image displayed on a display unit 130 of an information processing apparatus 100 according to an embodiment of the present disclosure.

FIGS. 4 to 6 are each an explanatory diagram showing an example of an image displayed on the display unit 130 of the information processing apparatus 100 according to an embodiment of the present disclosure. Hereinafter, with reference to FIGS. 4 to 6, display of the moving image in which the information generated by the information processing apparatus 100 is reflected is explained.

FIGS. 4 to 6 each show a situation where the information generated from the metadata overlaps a moving image 150 taken by the imaging apparatus 10 and the information and the moving image are displayed on the display unit 130. The moving image 150 taken by the imaging apparatus 10 includes a picture of the athlete 1 playing tennis with the racket 3.

In the examples shown in FIGS. 4 to 6, information generated by the information processing apparatus 100 is reflected in display of the moving image, the information including a degree of how close a ball position when the racket 3 hits the ball is to a point where the ball is hit most effectively (so-called sweet spot), power when the athlete 1 hits the ball with the racket 3, and a ball spin rate when the athlete 1 hits the ball with the racket 3.

Moreover, in the examples shown in FIGS. 4 to 6, the information generated by the information processing apparatus 100 is reflected in display of the moving image 150, the information including a time axis in which a point of time when the athlete 1 hits a ball with the racket 3 is displayed.

In the following explanation, information generated from the metadata to overlap the moving image 150 is also referred to as hit information.

Details of a display example of the moving image in which the information generated in Step S103 by the information processing apparatus 100 is reflected are explained. In an image displayed on the display unit 130 of the information processing apparatus shown in each of FIGS. 4 to 6, a reference sign 151 represents information indicating a ball position when the racket 3 hits a ball. A dark portion represents a probable place where the ball has actually hit, and a possibility that the ball has hit a place decreases with lightening color.

Reference sign 152 represents information indicating how close a position where the ball has hit is to the sweet spot. Reference sign 153 represents information indicating power when the athlete 1 hits the ball with the racket 3. Reference sign 154 represents information indicating a ball spin rate when the athlete 1 hits the ball with the racket 3.

Each information represented by the reference signs 152, 153, and 154 indicates that the position where the ball has hit is close to the sweet spot, the power is high, or the ball spin rate is high, as the number of blocks in a frame increases.

Reference sign 155 represents information indicating a time axis in which points of time when the athlete 1 hits the ball is displayed. With regard to a rectangle represented by the reference sign 155, the left periphery represents a starting point of the moving image 150, and the right periphery represents an end point of the moving image 150. Reference sign 156 is a bar representing a playback position. When the moving image is played back, the bar moves from the left periphery to the right periphery in the reference sign 155 under control of the display control unit 120. Accordingly, in chronological order, FIG. 5 comes after FIG. 4, and FIG. 6 comes after FIG. 5.

Reference sign 157 represents a timing when the athlete 1 has hit the ball with the racket 3. When the moving image is started to played back, the bar represented by the reference sign 156 is started to move from the left periphery toward the right periphery, and the bar represented by the reference sign 156 reaches a time point of the bar represented by the reference sign 157, a scene where the athlete 1 is hitting the ball with the racket 3 is shown as the moving image 150. The display control unit 120 may control the bar represented by the reference sign 157 in a manner that a color type or a color density changes depending on a shot type of an athlete. For example, the display control unit 120 turns a bar represented by the reference sign 157 into red in a case where a shot of the athlete 1 is a forehand stroke, turns a bar represented by the reference sign 157 into green in a case of a backhand stroke, turns a bar represented by the reference sign 157 into right blue in a case of a forehand slice, or turns a bar represented by the reference sign 157 into yellow in a case of a backhand slice.

Reference sign 158 represents a shot type when the athlete 1 has hit the ball with the racket 3. In FIG. 4, the athlete 1 shown in the moving image 150 hits the ball using the forehand stroke. Accordingly, the reference sign 158 shows the forehand stroke. In FIG. 5, the athlete 1 shown in the moving image 150 hits the ball using the forehand slice. Accordingly, the reference sign 158 shows the forehand slice. In FIG. 6, the athlete 1 shown in the moving image 150 hits the ball using the backhand slice. Accordingly, the reference sign 158 shows the backhand slice.

As described above, the display control unit 120 generates the information from the metadata, the information is displayed on the display unit 130, and the information processing apparatus 100 according to an embodiment of the present disclosure can help the athlete 1 who plays tennis to improve skills in tennis. Note that, the display control unit 120 may control the information to overlap the moving image 150 in a manner that the information is hidden or a position of the information is moved so as not to overlap the athlete 1.

Figure 7:
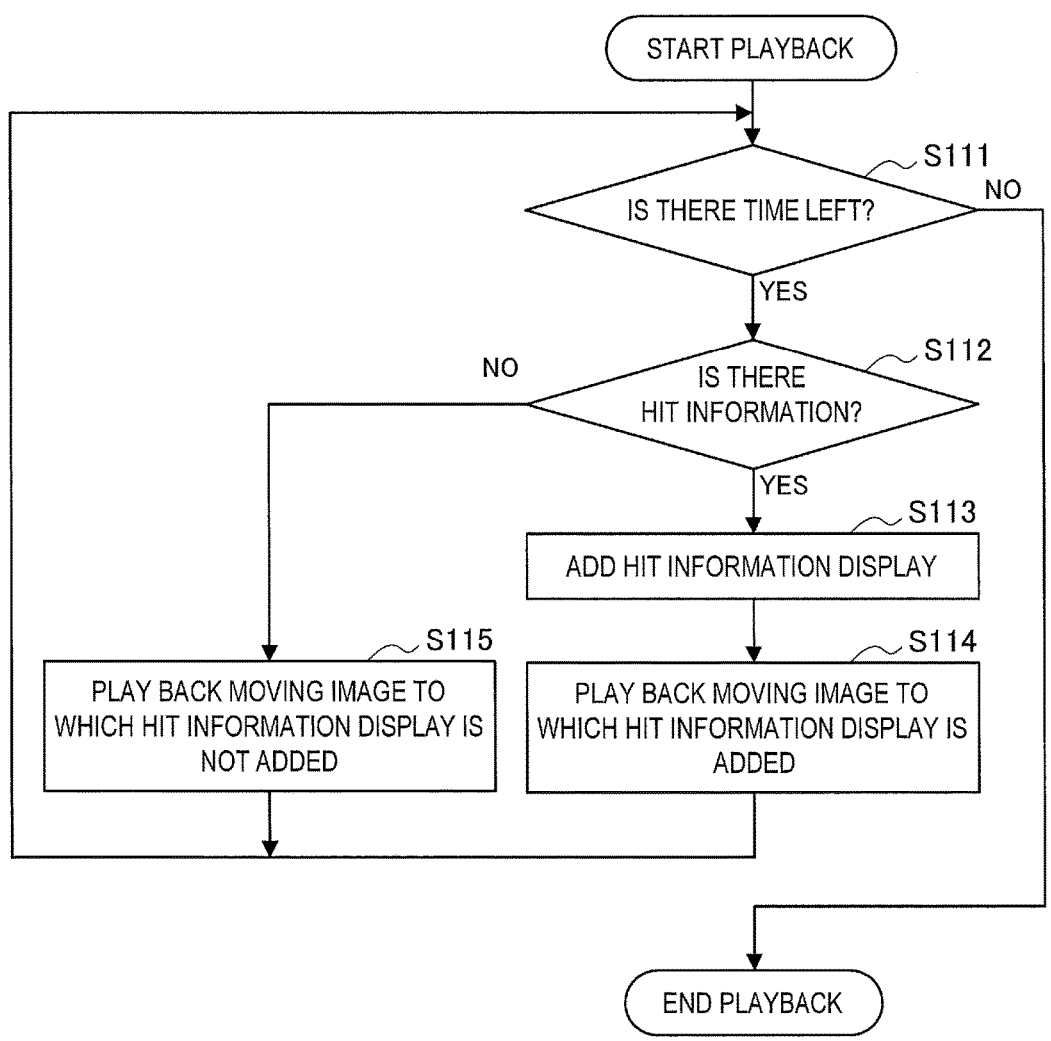
FIG. 7 is a flowchart showing an operation example of an information processing apparatus 100 according to an embodiment of the present disclosure.

FIG. 7 is a flowchart showing the operation example of the information processing apparatus 100 according to an embodiment of the present disclosure. FIG. 7 shows addition of hit information to the moving image to be played back when the moving image is played back such as shown in FIGS. 4 to 6. Hereinafter, with reference to FIG. 7, the operation example of the information processing apparatus 100 according to an embodiment of the present disclosure is explained.

First, in the information processing apparatus 100, when the display control unit 120 plays back the moving image, the display control unit 120 determines whether there is time left (Step S111). If there is no time left, the information processing apparatus 100 ends a playback process of the moving image.

On the other hand, if there is time left, the display control unit 120 of the information processing apparatus 100 subsequently determines whether there is hit information at a time of playback (Step S112). If there is the hit information at the time of playback as a result of the determination in Step S112, the information processing apparatus 100 causes the display control unit 120 to perform control in a manner that hit information display is added to the moving image to be played back (Step S113). Next, the information processing apparatus 100 causes the display control unit 120 to perform control in a manner that the moving image to which the hit information display is added in Step S113 is played back (Step S114).

On the other hand, if there is no hit information at the time of playback as a result of the determination in Step S112, the information processing apparatus 100 causes the display control unit 120 to perform control in a manner that a moving image to which the hit information display is not added is played back (Step S115).

As shown in FIGS. 4 to 6, by executing the operation in such a way, the information processing apparatus 100 according to an embodiment of the present disclosure can add the hit information at the time of playing back the moving image. As shown in FIGS. 4 to 6, by adding the hit information at the time of playing back the moving image, the athlete 1 who watches the moving image played back by the information processing apparatus 100 is expected to improve his skills.

2. HARDWARE CONFIGURATION EXAMPLE

The operation of the information processing apparatus 100 described above can be performed by using, for example, the hardware configuration of the information processing apparatus shown in FIG. 8. That is, the operation of the information processing apparatus 100 can be realized by controlling the hardware shown in FIG. 8 using a computer program. Additionally, the mode of this hardware is arbitrary, and may be a personal computer, a smart phone, a tablet device, a mobile information terminal such as a mobile phone, a PHS or a PDA, a game machine, a contact or non-contact IC chip, a contact or non-contact IC card, or various types of information appliances. Moreover, the PHS is an abbreviation for personal handy-phone system. Also, the PDA is an abbreviation for personal digital assistant.

As shown in FIG. 8, this hardware mainly includes a CPU 902, ROM 904, RAM 906, a host bus 908, and a bridge 910. Furthermore, this hardware includes an external bus 912, an interface 914, an input unit 916, an output unit 918, a storage unit 920, a drive 922, a connection port 924, and a communication unit 926. Moreover, the CPU is an abbreviation for central processing unit. Also, the ROM is an abbreviation for read only memory. Furthermore, the RAM is an abbreviation for random access memory.

The CPU 902 functions as an arithmetic processing unit or a control unit, for example, and controls entire operation or a part of the operation of each structural element based on various programs recorded on the ROM 904, the RAM 906, the storage unit 920, or a removable recording medium 928. The ROM 904 is a mechanism for storing, for example, a program to be loaded on the CPU 902 or data or the like used in an arithmetic operation. The RAM 906 temporarily or perpetually stores, for example, a program to be loaded on the CPU 902 or various parameters or the like arbitrarily changed in execution of the program.

These structural elements are connected to each other by, for example, the host bus 908 capable of performing high-speed data transmission. The host bus 908 is connected through the bridge 910 to the external bus 912 whose data transmission speed is relatively low, for example. Furthermore, the input unit 916 is, for example, a mouse, a keyboard, a touch panel, a button, a switch, or a lever. Also, the input unit 916 may be a remote control that can transmit a control signal by using an infrared ray or other radio waves.

The output unit 918 is, for example, a display device such as a CRT, an LCD, a PDP or an ELD, an audio output device such as a speaker or headphones, a printer, a mobile phone, or a facsimile, that can visually or auditorily notify a user of acquired information. Moreover, the CRT is an abbreviation for cathode ray tube. The LCD is an abbreviation for liquid crystal display. The PDP is an abbreviation for plasma display panel. Also, the ELD is an abbreviation for electroluminescence display.

The storage unit 920 is a device for storing various data. The storage unit 920 is, for example, a magnetic storage device such as a hard disk drive (HDD), a semiconductor storage device, an optical storage device, or a magneto-optical storage device. The HDD is an abbreviation for hard disk drive.

The drive 922 is a device that reads information recorded on the removable recording medium 928 such as a magnetic disk, an optical disk, a magneto-optical disk, or a semiconductor memory, or writes information in the removable recording medium 928. The removable recording medium 928 is, for example, a DVD medium, a Blu-ray medium, an HD-DVD medium, various types of semiconductor storage media, or the like. Of course, the removable recording medium 928 may be, for example, an electronic device or an IC card on which a non-contact IC chip is mounted. The IC is an abbreviation for integrated circuit.

The connection port 924 is a port such as an USB port, an IEEE1394 port, a SCSI, an RS-232C port, or a port for connecting an externally connected device 930 such as an optical audio terminal. The externally connected device 930 is, for example, a printer, a mobile music player, a digital camera, a digital video camera, or an IC recorder. Moreover, the USB is an abbreviation for universal serial bus. Also, the SCSI is an abbreviation for small computer system interface.

The communication unit 926 is a communication device to be connected to a network 932, and is, for example, a communication card for a wired or wireless LAN, Bluetooth (registered trademark), ANT (registered trademark), Zigbee (registered trademark), or WUSB, an optical communication router, an ADSL router, or a device for contact or non-contact communication. The network 932 connected to the communication unit 926 is configured from a wire-connected or wirelessly connected network, and is the Internet, a home-use LAN, infrared communication, visible light communication, broadcasting, or satellite communication, for example. Moreover, the LAN is an abbreviation for local area network. Also, the WUSB is an abbreviation for wireless USB. Furthermore, the ADSL is an abbreviation for asymmetric digital subscriber line.

3. CONCLUSION

According to an embodiment of the present disclosure as explained above, there is provided the information processing apparatus 100 that displays the moving image that the imaging apparatus 10 has taken and to which the metadata is attached, the metadata being generated by using the information detected by the sensor mounted on the racket 3 held by the athlete 1. According to an embodiment of the present disclosure, the information processing apparatus 100 acquires the metadata from the moving image, and generates information to be reflected in display of the moving image by using the acquired metadata.

According to an embodiment of the present disclosure, the information processing apparatus 100 acquires the metadata from the moving image, and generates information to be reflected in display of the moving image by using the acquired metadata. Accordingly, for example, in a case where a subject of the moving image plays sports, the information processing apparatus 100 can help the subject to improve skills in the sports.

Note that, according to an embodiment of the present disclosure, the information processing apparatus 100 that is a laptop computer adds information using the metadata to the moving image taken by the imaging apparatus 10. However, the present disclosure is not limited thereto. For example, it may be possible that a moving image that has been taken by the imaging apparatus 10 and to which metadata is added is uploaded to a server apparatus, and information using the metadata is added to the moving image taken by the imaging apparatus 10 in the server device that is an upload destination. In this case, the moving image to which the information is added in the server apparatus may be played back by a smartphone, tablet-type mobile terminal, or the like in addition to the information processing apparatus 100 that is the laptop computer.

Alternatively, such as the smartphone, a tablet, or a mobile phone, an information processing apparatus 100 integrated with the imaging apparatus 10 may takes an image, analyze sensor data, and attach metadata. Meanwhile, the present disclosure can be applied to a case where a sensor is mounted on a racket of badminton or table tennis. Alternatively, in a similar way, in addition to the racket, the present disclosure can be applied to a case where a sensor is mounted on a golf club, a baseball bat, a cricket bat, or shoes worn by an athlete at a time of a game.

In the above-described embodiment of the present disclosure, a situation where a single athlete is included in the moving image is explained. However, in a case where a plurality of people are included in the moving image, the information processing apparatus 100 may perform human detection, specify a person, explicitly show that display corresponds to which specified person, and display information generated from metadata. As such display corresponding to a person, the information processing apparatus 100 may display a name of the person in information to overlap a moving image, change color of information for each person, or cause a user to perceive that a detected person and an overlapping object are connected by overlapping a line connecting the detected person and the overlapping object. The name of the person may be stored in the storage unit 140 beforehand, and the display control unit 120 may acquire the corresponding name from the storage unit 140 by the human detection.

For example, it may not be necessary to chronologically execute respective steps in the process, which is executed by each apparatus of this specification, in the order described in the sequence diagrams or the flowcharts. For example, the respective steps in the process which is executed by each apparatus may be processed in the order different from the order described in the flowcharts, and may also be processed in parallel.

Furthermore, it becomes possible to generate a computer program which makes a hardware device, such as a CPU, ROM, and RAM incorporated in each apparatus demonstrate the functions equivalent to the configurations of the above described apparatuses. It becomes also possible to provide a storage medium which stores the computer program. In addition, respective functional blocks shown in the functional block diagrams may be constituted from hardware devices, so that a series of processing may be implemented by the hardware devices.

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

Additionally, the present technology may also be configured as below.

(1)

An information processing apparatus including:

a data acquiring unit configured to acquire content to which metadata is attached and the metadata attached to the content, the metadata being generated from data obtained from a sensor mounted on a subject; and a display control unit configured to reflect contents of the metadata acquired by the data acquiring unit in display of the content to which the metadata acquired by the data acquiring unit is attached.

(2)

The information processing apparatus according to (1), wherein the metadata is generated from data obtained from a sensor mounted on equipment used by the subject, and wherein the display control unit reflects, in display of the content, information on a situation where the subject uses the equipment.

(3)

The information processing apparatus according to (1) or (2), wherein, when the contents of the metadata are reflected in display of the content, the display control unit controls the display in a manner that the contents of the metadata are prevented from overlapping the subject.

(4)

The information processing apparatus according to any one of (1) to (3), wherein, in a case where the content includes a plurality of people as the subject, the display control unit reflects the contents of the metadata in display of the content in a manner that the contents of the metadata associate with the respective people.

(5)

The information processing apparatus according to (4), wherein the display control unit reflects names of the people in display of the content.

(6)

The information processing apparatus according to (4) or (5), wherein, according to the people, the display control unit changes color of information generated from the contents of the metadata.

(7)

The information processing apparatus according to any one of (4) to (6), wherein the display control unit reflects, in display of the content, lines connecting the people with the information generated from the contents of the metadata.

(8)

An information processing method including:

acquiring content to which metadata is attached and the metadata attached to the content, the metadata being generated from data obtained from a sensor mounted on a subject; and reflecting contents of the acquired metadata in display of the content to which the acquired metadata is attached.

(9)

A recording medium having a computer program recorded therein, the program causing a computer to execute:

acquiring content to which metadata is attached and the metadata attached to the content, the metadata being generated from data obtained from a sensor mounted on a subject; and reflecting contents of the acquired metadata in display of the content to which the acquired metadata is attached.

REFERENCE SIGNS LIST 1, 2 athlete
3, 4 racket
10 imaging apparatus
100 information processing apparatus
110 data acquiring unit
120 display control unit
130 display unit
140 storage unit

The invention claimed is:

1. A non-transitory computer-readable medium having embodied thereon a program, which when executed by a computer causes the computer to execute a method, the method comprising:
   receiving content associated with metadata and the metadata which is generated from data obtained from a sensor mounted on a subject while performing one or more contacting strikes of a sports movement; and
   controlling a display of the received metadata and the received content,
   wherein the content includes a time axis along which one or more indicators are provided to indicate timing of the one or more contacting strikes of the sports movement, and the time axis includes a playback position indicator positioned at a point along the time axis that corresponds to a current playback position of displaying the content, the playback position indicator being controlled to move along the time axis in association with a progression of displaying the content, and
   wherein a color type or a color density of the time axis is changed depending on a type of the one or more contacting strikes of the sports movement.

2. The non-transitory computer-readable medium according to claim 1,
   wherein the subject is an equipment used by a user performing the sports movement, and
   wherein information on a situation where the equipment is used is controlled to be displayed with the content.

3. The non-transitory computer-readable medium according to claim 1,
   wherein the metadata is controlled to be displayed so as not to overlap with a part of the content.

4. The non-transitory computer-readable medium according to claim 1,
   wherein, in a case where the content includes a plurality of people as the subject, the metadata is controlled to be displayed with the content in a manner that the metadata is associated with the respective people.

5. The non-transitory computer-readable medium according to claim 4,
   wherein names of the people are controlled to be displayed with the content.

6. The non-transitory computer-readable medium according to claim 4,
   wherein, according to the people, a color of information generated from the metadata is changed.

7. The non-transitory computer-readable medium according to claim 4,
   wherein lines connecting the people with the information generated from the metadata are controlled to be displayed with the content.

8. The non-transitory computer-readable medium according to claim 1,
   wherein when the playback position indicator is positioned at a point along the time axis corresponding to a first indicator of the one or more indicators, the metadata are controlled to be displayed as information that is associated with the first indicator and obtained at a point in time corresponding to a display location of the first indicator upon the time axis.

9. The non-transitory computer-readable medium according to claim 1,
   wherein the activity is tennis.

10. The non-transitory computer-readable medium according to claim 1,
    wherein the received metadata are controlled to be displayed to include hit information that indicates the type of the one or more contacting strikes.

11. The non-transitory computer-readable medium according to claim 1,
    wherein the received metadata controlled to be displayed with the content further includes hit information that indicates contacting position or effectiveness of the one or more contacting strikes.

12. The non-transitory computer-readable medium according to claim 1,
    wherein the received metadata controlled to be displayed with the content further includes hit information that indicates both contacting position and effectiveness of the one or more contacting strikes, the indicated effectiveness including information regarding location of contact in respect to a predefined sweet spot.

13. The non-transitory computer-readable medium according to claim 12,
    wherein the information regarding location of contact in respect to the predefined sweet spot includes a distance from the contacting position on the equipment to the sweet spot.

14. The non-transitory computer-readable medium according to claim 1,
    wherein the metadata includes a time at which the data was obtained from the sensor.

15. The non-transitory computer-readable medium according to claim 1,
    wherein the time axis includes a starting point and an end point of the content.

16. An information processing apparatus comprising:
    circuitry configured to
      receive content associated with metadata and the metadata which is generated from data obtained from a sensor mounted on a subject while performing one or more contacting strikes of a sports movement, and
      control a display of the received metadata and the received content,
    wherein the content includes a time axis along which one or more indicators are provided to indicate timing of the one or more contacting strikes of the sports movement, and the time axis includes a playback position indicator positioned at a point along the time axis that corresponds to a current playback position of displaying the content, the playback position indicator being controlled to move along the time axis in association with a progression of displaying the content, and
    wherein a color type or a color density of the time axis is changed depending on a type of the one or more contacting strikes of the sports movement.

17. An information processing method comprising:
    receiving content associated with metadata and the metadata which is generated from data obtained from a sensor mounted on a subject while performing one or more contacting strikes of a sports movement; and
    controlling a display of the received metadata and the received content,
    wherein the content includes a time axis along which one or more indicators are provided to indicate timing of the one or more contacting strikes of the sports movement, and the time axis includes a playback position indicator positioned at a point along the time axis that corresponds to a current playback position of displaying the content, the playback position indicator being controlled to move along the time axis in association with a progression of displaying the content, and wherein a color type or a color density of the time axis is changed depending on a type of the one or more contacting strikes of the sports movement.

* * * * *